United States Patent
Martin et al.

(10) Patent No.: US 7,899,764 B2
(45) Date of Patent: Mar. 1, 2011

(54) MEDICAL ONTOLOGIES FOR MACHINE LEARNING AND DECISION SUPPORT

(75) Inventors: Huber Martin, Uttenreuth (DE); Alexey Tsymbal, Erlangen (DE); Sonja Zillner, München (DE)

(73) Assignee: Siemens Aktiengesellschaft, Munich (DE)

( * ) Notice: Subject to any disclaimer, the term of this patent is extended or adjusted under 35 U.S.C. 154(b) by 928 days.

(21) Appl. No.: 11/763,717

(22) Filed: Jun. 15, 2007

(65) Prior Publication Data

US 2008/0201280 A1     Aug. 21, 2008

(30) Foreign Application Priority Data

Feb. 16, 2007    (EP)    ................................. 07003309

(51) Int. Cl.
    *G06F 15/18* (2006.01)
(52) U.S. Cl. ....................................................... 706/12
(58) Field of Classification Search .................... 706/12
    See application file for complete search history.

(56) References Cited

U.S. PATENT DOCUMENTS

| | | | |
|---|---|---|---|
| 7,630,947 B2 * | 12/2009 | Pandya et al. .................. | 706/45 |
| 2003/0120133 A1 | 6/2003 | Rao et al. | |
| 2003/0120134 A1 | 6/2003 | Rao et al. | |
| 2003/0120458 A1 | 6/2003 | Rao et al. | |
| 2003/0126101 A1 | 7/2003 | Rao et al. | |
| 2003/0130871 A1 | 7/2003 | Rao et al. | |
| 2005/0209519 A1 * | 9/2005 | Krishnan et al. ............. | 600/437 |
| 2007/0094188 A1 | 4/2007 | Pandya et al. | |
| 2009/0012928 A1 * | 1/2009 | Lussier et al. ................. | 706/59 |

OTHER PUBLICATIONS

Neighborhood graph and learning discriminative distance functions for clinical decision support, Tsymbal, A.; Zhou, S.K.; Huber, M.; Engineering in Medicine and Biology Society, 2009. EMBC 2009. Annual International Conference of the IEEE Digital Object Identifier: 10.1109/IEMBS.2009.5333784 Publication Year: 2009 , pp. 5617-5620.*

Based on Ontology : Construction and application of Medical Knowledge Base, Xu Binfeng; Luo Xiaogang; Peng Chenglin; Huang Qian; Complex Medical Engineering, 2007. CME 2007. IEEE/ICME International Conference on Digital Object Identifier: 10.1109/ICCME.2007.4382013 Publication Year: 2007 , pp. 1586-1589.*

(Continued)

*Primary Examiner*—Michael Holmes
(74) *Attorney, Agent, or Firm*—Brinks Hofer Gilson & Lione (57) ABSTRACT

A medical ontology may be used for computer assisted clinical decision support. Multi-level and/or semantically grouped medical ontology is incorporated into a machine learning algorithm. The resulting machine-learnt algorithm outputs information to assist in clinical decisions. For example, a patient record is input to the algorithm. Based on the incorporated medical ontology, similarities are aggregated in different groups. An aggregate similarity of at least one group is a function of an aggregate similarity of at least another group. One or more similar patients and/or outcomes are identified based on similarity. Probability based outputs may be provided.

22 Claims, 3 Drawing Sheets

OTHER PUBLICATIONS

Clinical Decision Support System for Fetal Delivery Using Artificial Neural Network, Janghel, R.R.; Shukla, A.; Tiwari, R.; Tiwari, P.; New Trends in Information and Service Science, 2009. NISS '09. International Conference on Digital Object Identifier: 10.1109/NISS.2009.66 Publication Year: 2009, pp. 1070-1075.*

Localized Supervised Metric Learning on Temporal Physiological Data, Sun, Jimeng; Sow, Daby; Hu, Jianying; Ebadollahi, Shahram; Pattern Recognition (ICPR), 2010 20th International Conference on Digital Object Identifier: 10.1109/ICPR.2010.1009 Publication Year: 2010, pp. 4149-4152.*

Rao, et al., "Clinical and Financial Outcomes Analysis with Existing Hospital Patient Records", SIGKDD '03, Aug. 24-27, 2003, Washington, D.C., USA 10 pgs.

International Statistical Classification of Diseases and Related Health Problems, 10$^{th}$ Revision, Version for 2006, Feb. 22, 2007 www.who.int/classifications/apps/icd/icd10online/navi.htm.

Melton, et al., "Inter-patient distance metrics using SNOMED CT defining relationships", J. of Biomedical Informatics, 39 (2006), pp. 697-705.

Camps-Valls, et al., "Composite Kernels for Hyperspectral Image Classification", IEEE Geoscience & Remote Sensing Letters, vol. XX, No. Y, Month Z, 2005, pp. 1-5.

Olivier Bodenreider, "The Unified Medical Language System (UMLS): integrating biomedical terminology", Nucleic Acids Research, 2004, vol. 32, Database Issue D-267-D270.

Rosse, et al., "A reference ontology for biomedical informatics: the Foundation Model of Anatomy", J. of Biomedical Informatics, 36 (2003), pp. 478-500.

Stearns, et al. "Snowmed Clinical Terms: Overview of the Development Process and Project Status", In Proceeding of AMIA Symposium, 2001, pp. 662-666.

* cited by examiner

Fig. 1

| Name | Domain | Size | Format | Type | Licensing | Institution |
|---|---|---|---|---|---|---|
| UMLS | Biomedical and Health domain | 900 000 concepts | Relational files, OO-model, web access | Meta-Thesarus | UMLS Licensing | NLM/NIH |
| SNOMED CT | Healthcare Terms | 400 000 concepts | proprietary format, web access | Thesaurus | Commerical & in UMLS | SNOMED International |
| ICD | Diseases and Injuries | 60 000 concepts | book format, proprietary format, web access | Taxonomy | Commerical & in UMLS | WHO |
| FMA | Human Anatomy | 70 000 concepts | Protege-Frames, web access | Ontology | Free | Univ. of Washington |
| MeSH | Medical Terms | 22500 concepts | XML, ASCII, Tree, MARC, RDF/OWL, web access | Thesaurus | Free | NLM/NIH |
| Gene Ontology | Genetics | 22 000 concepts | OWL, XML, OBO, Text, MySQL, web access | Thesaurus | Free | Collaborative |
| MGED | Microarray Experiments | 230 concepts | OWL | Ontology | Free | MGED Society |
| BioPax | Biological Pathway Data | 40 concepts | OWL | Ontology | Free | Collaborative |

MEDICAL ONTOLOGIES FOR MACHINE LEARNING AND DECISION SUPPORT

RELATED APPLICATIONS

The present patent document claims the benefit of the filing date under 35 U.S.C. §119(a) of European Patent Application No. EP07003309, filed Feb. 16, 2007.

BACKGROUND

The present embodiments relate to machine learning and application of machine-learnt algorithms. In particular, computer assisted medical decision support incorporates a medical ontology.

Ontologies and machine learning constitute two technologies for domain-specific knowledge extraction actively used in knowledge-based systems. Ontologies are a result of the knowledge elicitation process from an expert by knowledge engineers, and data is not necessarily involved in this process. Machine learning is data-driven. The search for patterns is usually automatic and may not involve substantial interaction with the expert. The aim of these two technologies is generally the same—the extraction of useful knowledge.

By establishing an explicit formal specification of the concepts in a particular domain and relations among them, ontologies provide the basis for reusing and integrating valuable domain knowledge within applications. Medical ontologies provide information associated with one or more diseases and numerous medically relevant concepts (e.g., laboratory and diagnostic procedures; physiologic, biologic, genetic, molecular functions; organs and body parts; diseases, symptoms, and medical findings; and others). Different relationships between concepts are reflected by the medical ontology. For example, different names for a same disease are provided in an "IS A" type relationship. Related morphologies (e.g., inflammation) and body location are other types of relationships in the medical ontology. Medical ontologies may also contain various terms associated to a medical concept representing the same (or similar) meaning for the concept.

Medical ontologies provide information for computer assisted medical decision support. Computer assisted medical decision support systems may be deterministic. For example, a rule-based system alerts clinicians to drug-drug interaction. The rules are determined manually from the medical ontology.

Machine learning algorithms are applied in order to extract useful knowledge in different problem domains by searching for interesting patterns (dependencies) in large volumes of data. The principle of instance (patient) similarity is the basis for many machine learning algorithms. The main assumption in supervised, unsupervised and semi-supervised machine learning algorithms is that the instances of the same class (cluster) are more similar to each other than the instances of different classes (clusters).

Traditional machine learning algorithms are not able to incorporate background domain knowledge, but instead work with a sequence of instances, where each instance is represented by a single feature (attribute) vector describing the instance.

The use of ontologies in data mining is focused on homogeneously represented cases and use taxonomic distance and ontologies with "is_a" relations. These techniques are not particularly suitable for mining complex medical data. The focus in the so-called knowledge-intensive similarity measures is on creating a customised distance function for each particular feature, and not on the total aggregated distance (similarity). One-level feature grouping and either building a separate model for each semantic group (ensemble learning) or aggregating partial distances calculated within each group have been proposed.

BRIEF SUMMARY

By way of introduction, the preferred embodiments described below include methods, systems, and instructions for use of a medical ontology for computer assisted clinical decision support. A multi-level and/or semantically grouped medical ontology is incorporated into a machine learning algorithm. The resulting machine-learnt algorithm outputs information to assist in clinical decisions. For example, a patient record is input to the algorithm. Based on the incorporated medical ontology, similarities are aggregated in different groups. An aggregate similarity of at least one group is a function of an aggregate similarity of at least another group. One or more similar patients and/or outcomes are identified based on the final aggregated similarity. Alternatively or additionally, probability based outputs may be provided.

In a first aspect, a method is provided for use of a medical ontology for computer assisted clinical decision support. A medical ontology indicates one or more semantic groupings of features. A processor learns to identify at least one similar patient record from a set of patient records. The learning is a function of the one or more semantic groupings of features of the medical ontology. Information derived from the learning is output.

In a second aspect, a system is provided for use of a medical ontology for computer assisted clinical decision support. A memory is operable to store a machine-learnt algorithm. The machine-learnt algorithm integrates a multi-level medical ontology. The multi-level medical ontology has a hierarchal node structure defining relative contribution of features at different levels of the multi-level medical ontology. A processor is operable to apply the machine-learnt algorithm to a medical record of a patient.

In a third aspect, a computer readable storage media has stored therein data representing instructions executable by a programmed processor for computer assisted clinical decision support with a medical ontology using machine learning. The storage media include instructions for incorporating, into a machine learning algorithm, domain knowledge from a medical ontology describing interrelations between features, searching, with the machine learning algorithm, a sequence of instances where each instance is represented by at least one single feature vector describing the instance, the searching including aggregating similarities in different groups, an aggregate similarity of at least one group being a function of an aggregate similarity of at least another group, and identifying, in response to the searching, a similar instance with the machine learning algorithm.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Ontologies and machine learning constitute two major technologies for domain-specific knowledge extraction used in knowledge-based systems (computer assisted clinical decision support systems) of different kinds, including expert systems, decision support systems, and knowledge discovery systems. In biomedicine, relevant data are often naturally complex having large dimensionality and including heterogeneous features. A large body of knowledge is available in the form of ontologies. One approach for improving the performance of machine learning algorithms integrates the knowledge provided by ontologies.

The machine learning may be used for probabilistic decision support, distance or similarity identification decision support, or data mining decision support. For learning to identify similar patients and outcomes, similarity (distance) is redefined for complex heterogeneous data by incorporating available ontological knowledge, creating a bridge between the two technologies. The medical ontology may be used to redefine probability related information for probability based machine learning.

Constraints provided by ontological domain knowledge are incorporated into the machine learning. Instead of simply providing the machine learning algorithm with unrelated features in the form of a single vector or a vector set, the features are semantically enhanced by integrating the graph structures of relevant domain ontologies. The performance of the machine learning algorithms may be improved by incorporating knowledge provided by domain ontologies. For example, the predictive accuracy of k-nearest neighbour classification may be improved.

An ontology describing the interrelations between the features in a machine learning problem may be presented to the user of a knowledge-based system. The displayed ontology allows for feature control and manipulation for decision support. The ontology may not be fixed, but may be integrated as a flexible wrapper for more efficient machine learning and knowledge discovery. Changes in the feature ontology, initiated by the user and leading to an increase in machine learning performance, may serve as an important source of knowledge in the domain.

Figure 1:
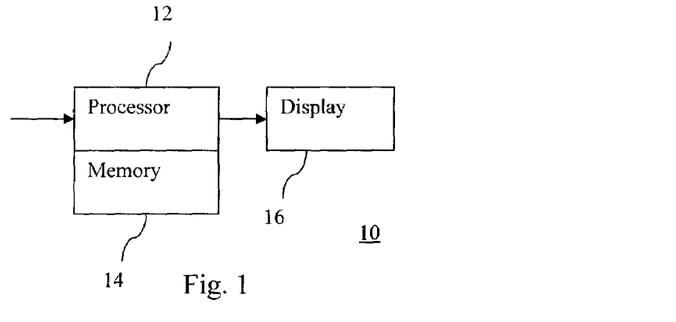
FIG. 1 is a block diagram of one embodiment of a system for use of a medical ontology for computer assisted clinical decision support.

FIG. 1 shows a system 10 for use of a medical ontology in computer assisted clinical decision support. The system 10 includes a processor 12, a memory 14, and a display 16. Additional, different or fewer components may be provided, such as a user input device. The system 10 is a personal computer, workstation, medical diagnostic imaging system, network, or other now known or later developed system for providing decision support. For example, the system is a workstation for analyzing a medical ontology, training a mining or searching classifier, or generating domain knowledge.

As another example, the system 10 is a computer aided diagnosis system incorporating information from a medical ontology. Automated assistance is provided to a physician for identifying similar patient records. Assistance is provided for diagnosis of heart diseases, breast cancer, lung cancer, other disease, symptoms, causes, effects, or other medically useful information. The automated assistance is provided after subscription to a third party service, purchase of the system 10, purchase of software, or payment of a usage fee. The system 10 is used for training an algorithm, for applying a trained algorithm, or both.

The processor 12 is a general processor, digital signal processor, application specific integrated circuit, field programmable gate array, analog circuit, digital circuit, combinations thereof, or other now known or later developed processor. The processor 12 may be a single device or a combination of devices, such as associated with a network or distributed processing. Any of various processing strategies may be used, such as multi-processing, multi-tasking, parallel processing, or the like. The processor 12 is responsive to instructions stored as part of software, hardware, integrated circuits, firmware, micro-code or the like.

The processor 12 operates to create, read, receive input about, or otherwise use a medical ontology and/or to apply a knowledge base or trained classifier based on a medical ontology. In one embodiment, the processor 12 provides a user interface for manually or semi-automatically creating a medical ontology from one or more sources of information. An expert's or experts' knowledge and/or intuition may be used to map the medical ontology. For example, a single medical ontology for a given decease is created from one or more sources of information, such as medical ontologies for different types of data (e.g., clinical, imaging, and/or genetics). The medical ontology is developed for a desired classification task.

Data mining or machine learning are alternatively or additionally used to identify and/or refine features, portions, groupings, or the complete medical ontology. If sufficient test data is available, data-driven feature ontology refinement may be applied, taking the expert ontology as a starting point in the search. Various relations available in existing ontologies may be incorporated in the distance calculation or learning. For example, many ontologies include information about correlation between relevant features.

Any now existing or later developed medical ontologies may be used. Clinical and biomedical applications often have to deal with large volumes of complex information originating from different sources, with different structures, and with different semantics. Clinical and biomedical information are often structured to produce a vast number of standards and conceptual vocabularies that are reused in various medical applications. The information may be semantically integrated and enhanced. There exists a variety of knowledge organisation systems that can be used for capturing semantic knowledge in a medical ontology, including taxonomies, thesauri, and other ontologies. These knowledge organization systems express, either implicitly or explicitly, a more or less detailed semantic model.

A taxonomy establishes a classification hierarchy of terms. Similar objects are subsumed under distinct classes and subclasses.

Thesauri provide an additional source for refining established classification hierarchies. Thesauri provide a fixed set of predefined relations between concepts, enabling, for instance, the specification of similar or synonymic concepts.

By specifying a terminology of a particular domain, thesauri allow for the sophisticated and detailed annotation of objects of interest.

An ontology may provide an explicit, formal specification of a shared conceptualisation. Through the specification of rules, ontologies enable the formulation of constraints, negations, logical functions, and/or mathematical operations. As taxonomies and thesauri are less expressive than ontologies, their captured content may be represented with ontological structures.

Figure 2:
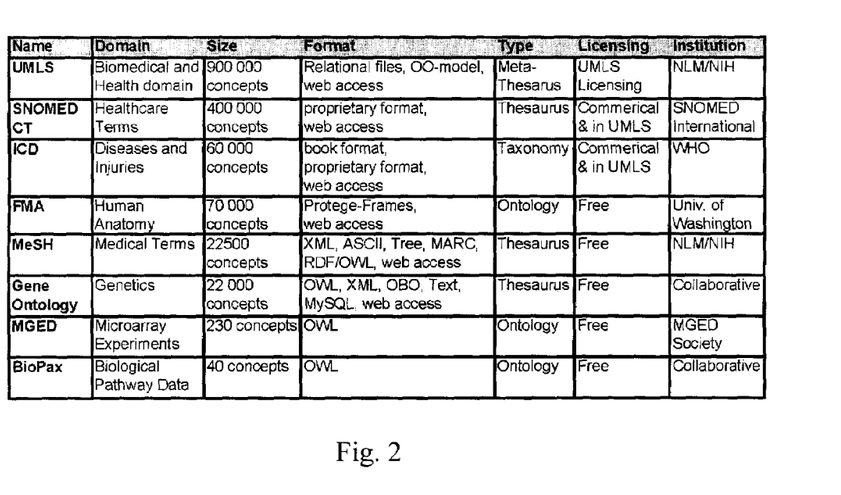
FIG. 2 is a table of example medical ontologies.

In the domain of healthcare and biomedical informatics, a number of different knowledge repositories have been developed. FIG. 2 shows an overview of relevant medical knowledge bases ordered by their size, i.e. the number of concepts or features. As one can see, the knowledge bases vary in size (from 900,000 in UMLS to 40 in BioPax), in the way of knowledge organisation (ontology, meta-thesaurus, thesauri, and taxonomy), in the covered subject domain, and in the format.

The Unified Medical Language System (UMLS) from the US National Library of Medicine (NLM) is a terminology integration project. It is a controlled compendium of medical vocabularies enhanced by mappings between them, with over 900 thousand concepts and 12 million relations between them. UMLS has three major components: the UMLS Metathesaurus of interrelated biomedical concepts integrating more than 60 families of biomedical vocabularies; the UMLS Semantic Network providing high-level categories for classifying every concept from the Meta-thesaurus; and the SPECIALIST lexicon yielding lexical resources and programmes for generating lexical variants of biomedical terms that enable the identification of lexically similar concepts.

The International Classification of Diseases (ICD) is published by the World Health Organization (WHO). Known diseases and other health-related problems are classified. The ICD enables the storage, retrieval and statistical analysis of diagnostic information. It is a taxonomy covering approximately 60 thousand concepts organised in 22 chapters of different classes of diseases. Similar diseases are subsumed in classes, and infrequent diseases are sometimes combined without indicating profound similarity.

Medical Subject Headings (MeSH) is a thesaurus used for indexing and annotating journal articles and books in the PubMed database of biomedical literature. A set of polyhierarchically structured concepts provide the basis for searching annotated medical literature at various levels of specificity. MeSH is created and maintained by the US National Library of Medicine (NLM). The MeSH Thesaurus establishes approximately 22,500 concepts (e.g., Disease, Cardiovascular Disease, Congenital Heart Defect, Atrial Septal Defect) and 83 qualifiers (e.g., Diagnose or Ultrasonography). Both concepts and qualifiers are hierarchically structured ranging from the most general to the most specific ones. The qualifiers allow for addressing a particular view of a concept, e.g. by attaching the qualifier Ultrasonography to the concept Atrial Septal Defect (ASD), one can emphasise the ultrasonography-related diagnostic aspects of ASD.

The Systematised Nomenclature of Medicine Clinical Terms (SNOMED CT) is a thesaurus of healthcare terms, covering clinical data for various diseases, clinical findings, and procedures. SNOMED CT is supported and maintained by SNOMED International, a division of the College of American Pathologists (CAP). It covers approximately 400 thousand concepts with formal logic-based definitions organised in 18 top-level hierarchies. Besides the classical "is-a" relations, it specifies more than 50 other relation types and encompasses more than 900 thousand instantiated relations.

The Gene-Ontology (GO) project is a collaborative effort to provide a set of structured vocabularies for labelling gene products in different databases. Aiming to establish a controlled vocabulary for describing the functions of genes in a species-independent manner, the GO has three independent vocabularies establishing terms for annotating molecular functions, cellular components, and biological processes in gene products. In short, molecular functions detail what a gene product does at the biochemical level, biological processes capture broad biological objectives, and cellular components specify the location of a gene product within cellular structures and within macromolecular complexes. Approximately 22 thousand concepts are organised as a directed acyclic graph, i.e. a hierarchical structure with concepts having one or more parents, and with two relations, "is-a" and "part-of", linking the concepts. The GO specifies no associative relations across its three hierarchies.

The Microarray Gene Expression Data (MGED) ontology provides standard terms for the annotation of microarray experiments. The ontology was created and is maintained by the MGED Society, an international organisation of biologists, computer scientists, and data analysts whose goal is to facilitate the sharing of microarray data generated by functional genomics and proteomics experiments. It encompasses 229 concepts and 110 properties. The concepts are defined and structured by formal-logic-based constraints, such as existential restrictions (specifying the existence of at least one relation of a given property to an individual being a member of a specific concept). MGED contains 658 instantiated concepts covering terms that are common to many microarrray experiments.

The Biological Pathway Exchange (BioPAX) project provides a common exchange format for biological pathway data, capturing the key elements of data models from a wide range of popular pathway databases. The established BioPax ontology covers metabolic pathway information, molecular interactions, protein post-translational modifications, and supports the Proteomics Standards Initiative (PSI). To cope with the complexity of pathway data, the BioPAX uses a multi-level development approach, i.e. BioPAX Level 1 is focused on the representation of metabolic pathway data, Level 2 expands the scope of Level 1 by including the representation of molecular binding interaction and hierarchical pathways, and further levels are also planned. The BioPAX Level 2 establishes 40 concepts and 33 properties.

The Foundational Model of Anatomy (FMA) is a comprehensive ontology of human "canonical" anatomy. It maintained by the School of Medicine of the University of Washington and the US National Library of Medicine (NLM). Beside the specification of anatomy taxonomy, i.e. an inheritance hierarchy of anatomical entities, the FMA provides definitions for conceptual attributes, part-whole, location, and other spatial associations of anatomical entities. By additionally allowing for attributing relations (i.e. relations can be described in more detail by attaching additional attributes), FMA specifies relations and, thus, can cope with the requirements for the precise and comprehensive capturing of the structure of the body. FMA covers approximately 70 thousand distinct anatomical concepts and more than 1.5 million relations instances from 170 relations types.

One ontology may be used for one type of information, such as symptoms, and another ontology used for another type of information, such as "IS A" relationships. One ontology may be used for one disease, and another ontology may be used for another disease. A plurality of ontologies may be used for the same disease and/or types of relationships. In the examples herein, the ontologies are used for disease specific decision support, but the ontologies may be used for symptom, cause, effect, signs, other concepts, or other features for analysis.

Figure 4:
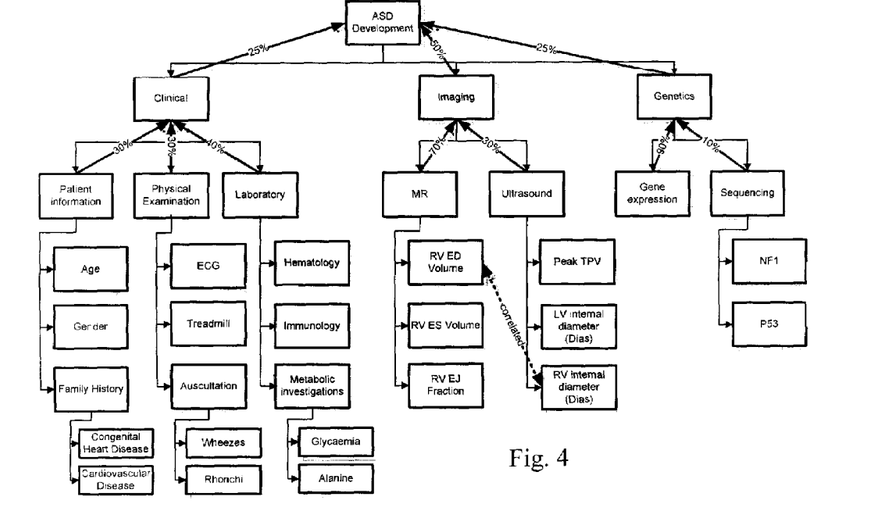
FIG. 4 is a graphical representation of one embodiment of a multi-level medical ontology with relatively weighted semantic groupings.
Figure 5:
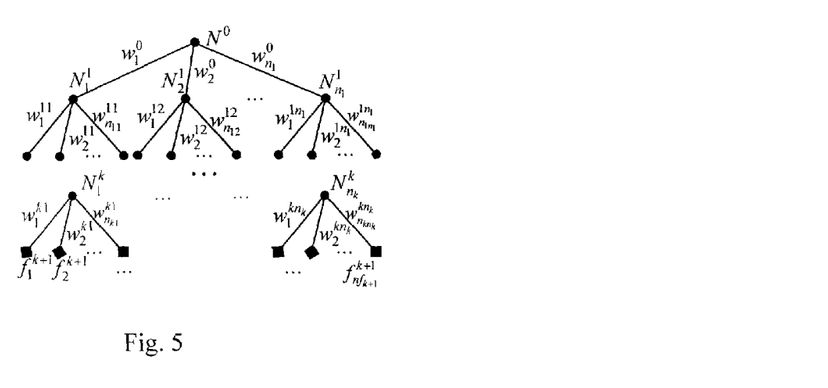
FIG. 5 is a graphical representation of another embodiment of a multi-level medical ontology.

The processor 12 may analyze and/or incorporates the ontology by searching for terms with specific relationships. For example, a programmer constrains machine learning based on the medical ontology. Medical ontologies are provided in a structured format, with different links between different terms. FIGS. 4 and 5 show example ontologies. FIG. 4 is an ontology for ASD development. Different semantic groupings are provided at different levels. For example, features associated with clinical, imaging, and genetics are grouped at one level into separate branches. At a lower level, further semantic groups may be provided. For example within the imaging group, magnetic resonance (MR) and ultrasound semantic groupings are formed. The features associated with MR imaging of interest to ASD development are shown as RV ED Volume, RV ES Volume and RV EJ Fraction. Other features may be included within any semantic grouping based on expertise and/or machine learning to identify significant, available, or possibly available features.

In the example of FIG. 4, the medical ontology is derived from different ontologies, such as a genetics ontology, an imaging ontology, and a clinical ontology. Only one ontology or derivation from other sources than an ontology may be used. The processor 12 and/or experts create a class specific medical ontology based on semantic groupings. For automated creation, the relationships used in any ontology may be used to establish semantic groupings, such as direct or "IS A" type relationships, site or body location relationships, morphology relationships, or other associations (e.g., a cause, an effect, a symptom, a sign, drugs, tests, or a related disease). For example, diabetes may be shown as related to or connected with heart failure, but is not the same or an "IS A" relation. Diabetes may be related since a person with diabetes is more likely to have heart failure than a person without diabetes.

As shown in FIG. 5, the semantic groupings provide nodes in a hierarchal medical ontology. Nodes at different levels may be responsive to or a function of nodes at other or the same levels. Any node may be responsive to one or more features. In the example of FIG. 4, the lowest level semantic groupings include features. However, higher-level semantic groupings may also include features, such as associated with a feature and child nodes being aggregated into a given node.

The processor 12 learns from a data set. Any now known or later developed machine learning algorithm may be used, such as discussed below for FIG. 3. Alternatively, the processor 12 applies a machine-learnt algorithm. The processor 12 applies the machine-learnt algorithm to search for or identify one or more similar patient records from a set of patient records. Alternatively or additionally, the matrices or other representation of the algorithm are applied to data of a patient record to indicate a probability of membership in the class defined by the ontology (e.g., probability of a specific disease). In another additional or alternative embodiment, the processor 12 may perform data mining based on the ontology. For example, the data mining, ontology creating, probability model creation, or probability model application disclosure in U.S. Published Patent Application No. 2007/0094188, the disclosure of which is incorporated herein by reference, is used.

In one embodiment for mining, the processor 12 is operable to apply a mining engine to a medical record. The mining engine uses the domain knowledge base extracted from the medical ontology. For example, a variable is assigned to each of the associated terms from the knowledge base. The mining engine searches for the associated terms in structured and/or unstructured portions of the medical record. In one embodiment, the mining engine is part of the REMIND (Reliable Extraction and Meaningful Inference from Non-structured Data) system, such as described in U.S. Publication Nos. 2003/0120458, 2003/0120133, 2003/0120134, 2003/0126101 or 2003/0130871, which are incorporated herein by reference. REMIND is a Bayesian framework that integrates and blends structured and unstructured clinical data in patient records to automatically create structured clinical data as an output. This structuring allows existing patient records to be mined for quality assurance, regulatory compliance, diagnosis assistance, and to relate financial and clinical factors. The mining engine may output any matching terms.

The mining engine may further infer a patient state as a function of the matched associated terms and corresponding probabilities of the associated terms indicating the patient state. The processor 12 applies the model generated, in part, from the ontology information. The results of the data mining are applied as inputs to the model. Similar patient records, the patient state, or other information is inferred based on training with ontology information. In alternative embodiments, the classifier is applied without the data mining, such as using manual input, or without mining unstructured data, such as using a structured input data set acquired without data mining based on ontology information.

In one embodiment for similarity determination, the processor 12 applies the machine-learnt algorithm to a medical record of a patient. Data for features identified in the medical ontology are extracted from the patient record or input into the trained algorithm. This data is used as inputs to the trained algorithm. The trained algorithm aggregates the contributions of these features based on the incorporated medical ontology. For example, distances or similarities for each feature from the patient record to other patient records are determined. The aggregation determines an average or other representation of distance from each of the previous patient records. Alternatively or additionally, the aggregation identifies only patient records with sufficient similarity for each of the features and/or nodes included in a given semantic grouping. As these records are aggregated, the number of qualifying (sufficient similarity) records is reduced.

The similarities in each semantic grouping are combined to aggregate a contribution of the features for each node. The process operates from the extremities, bottom, or other location within the multilevel framework provided by the ontology, such as aggregating for each lowest level node or nodes with only features. The similarities for higher-level nodes are then aggregated. For example, the similarity values for different children nodes are averaged or weighted and summed. Different semantic groupings may be weighted more heavily. A final similarity to each stored record or groups of records is determined from a final aggregate. The most or sufficiently similar previous medical records are identified by the machine-learnt algorithm as a function of the multi-level medical ontology and/or semantic groupings.

Medicine is a domain where large complex heterogeneous data sets are commonplace. Today, a single patient record may include, for example, demographic data, familiar history, laboratory test results, images (including echocardiograms, MRI, CT, angiogram etc), signals (e.g. EKG), genomic and proteomic samples, and history of appointments, prescriptions, and interventions. Not all of this data may be relevant for a particular class, but may contain important information for decision support. The processor 12 uses the machine-learnt algorithm and resulting incorporation of the medical ontology to extract and/or aggregate relevant similarity information from a patient record.

The memory 14 is a computer readable storage media. Computer readable storage media include various types of volatile and non-volatile storage media, including but not limited to random access memory, read-only memory, programmable read-only memory, electrically programmable read-only memory, electrically erasable read-only memory, flash memory, magnetic tape or disk, optical media and the like. The memory 14 may be a single device or a combination of devices. The memory 14 may be adjacent to, part of, networked with and/or remote from the processor 12.

The memory 14 may store the medical ontology. For example, a spreadsheet of the ontology terms and relationships is stored. The medical ontology may be scanned and/or OCRd for storage into the memory. Alternatively, the memory 14 stores information extracted from the medical ontology, such as associated terms, relationships, domain knowledge or combinations thereof.

The memory 14 may store training data or data to be searched. The data is a collection of two or more previously acquired patient records. For example, hundreds, thousands or tens of thousands of patient records are obtained and stored. In one embodiment, the records are originally created as part of a clinical study. In other embodiments, the records are gathered independent of a clinical study, such as being collected from one or more hospitals. The previous patient records may include corresponding labels or ground truths.

Each data set includes extracted variables for a plurality of features. The different patient records have the same extracted features, but one or more patient records may have fewer or a greater number of features. Alternatively, one or more of the patient records includes information to be used for extracting features, such as including an image. Any format may be used for maintaining and storing the training data.

The memory 14 may store a patient record. The patient record is input manually by the user and/or determined automatically. The patient record may be formatted or unformatted. The patient record resides in or is extracted from different sources or a single source. The patient record includes variables available for a current patient. The variables correspond to features, such as medical history, pain indication, lump indication, age, genetic information, test results, family history, billing codes, medications, lab results, notes, text, or other sources of information. The patient record may include one or more images of a same or different type. The processor 12, a different processor, or the user may extract variables from the image. The variables correspond to features of the image. Any now known or later developed patient record format, features and/or technique to extract features may be used.

The memory 14 stores a machine-learnt algorithm. The trained classifier is a model, matrix, variables and weights, program code, search engine, software, firmware, instructions, logic, tools, or other format. The trained algorithm may identify a previous medical record similar to the medical record of a given patient. The machine-learnt algorithm integrates the multi-level medical ontology having a hierarchal node structure defining relative contribution of features at different levels of the multi-level medical ontology. The multi-level medical ontology includes features with common semantics for nodes, such as nodes with features for children, nodes with at least one other node for a child, or nodes with only other nodes for children.

The memory 14 may store a mining engine. The mining engine includes the domain-knowledge base created from a medical ontology or other knowledge base. The mining engine is operable to mine the medical record as a function of the domain-knowledge base. The mining engine searches in structured and/or unstructured data of the medical record. The mining engine searches based on the medical ontology.

The memory 14 may store a probabilistic or other graphic model having machine-learned probabilities derived, in part, from the medical ontology. The associated terms represent different relationships, such as terms associated through cause, effect, a different disease or combinations thereof for a disease. For each term or relationship between two terms, a probability is provided. The probabilities may be combined based on identified or input terms for a given patient to probabilistically reason a chance the patient has the disease. The probabilities may be based, at least in part, on semantic groupings.

More than one classifier or model may be stored, such as having different models for different combinations of available data. Alternatively, the model allows for missing information.

The memory 14 may be a computer readable storage media having stored therein data representing instructions executable by the programmed processor 12 for computer assisted clinical decision support with a medical ontology using machine learning. The memory 14 stores instructions for the processor 12. The processor 12 is programmed with and executes the instructions. The functions, acts, methods or tasks illustrated in the figures or described herein are performed by the programmed processor 12 executing the instructions stored in the memory 14. The functions, acts, methods or tasks are independent of the particular type of instructions set, storage media, processor or processing strategy and may be performed by software, hardware, integrated circuits, film-ware, micro-code and the like, operating alone or in combination. The instructions are for implementing the processes, techniques, methods, or acts described herein, such as associated with FIG. 3.

The display 16 is a CRT, monitor, flat panel, LCD, projector, printer or other now known or later developed display device for outputting determined information. For example, the processor 12 causes the display 16 at a local or remote location to output data indicating identification of similar medical records, information from similar medical records, mining results, a possible diagnosis, a probability associated with one or more possible diagnoses, an image with marked locations of interest, medical record information supporting a probability or inference, or other medical decision assistance associated with the current patient record. The output may be stored with or separate from the patient record.

In one embodiment, the display 16 displays a representation of the multi-level medical ontology. The display may be for informational purposes, such as providing aggregate similarities for different semantic groupings. The display may be part of a user interface allowing the user to edit the medical ontology. For example, the user changes a relative weight for a node or grouping, adds or removes nodes and/or features, or makes other changes.

Figure 3:
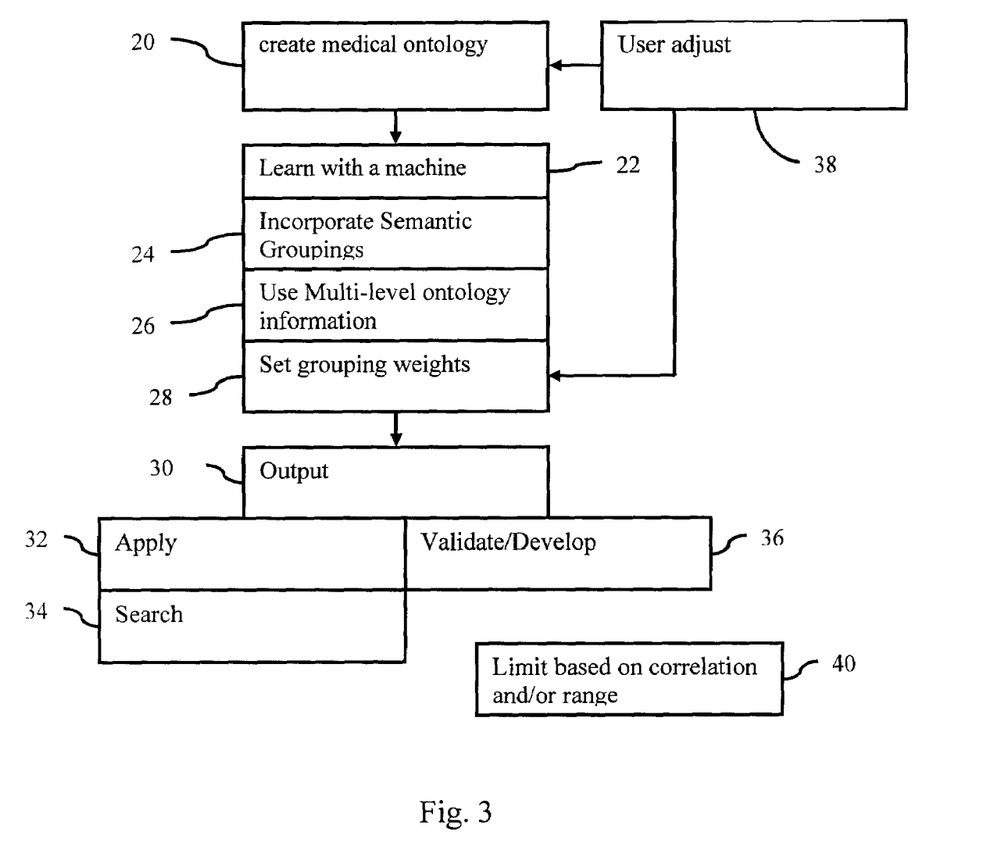
FIG. 3 is a flow chart diagram showing one embodiment of a method for use of a medical ontology for computer assisted clinical decision support.

FIG. 3 shows a method for use of a medical ontology for computer assisted clinical decision support. The method is implemented using the system 10 of FIG. 1 or a different system. Additional, different or fewer acts than shown in FIG. 3 may be provided. For example, act 22 is performed without act 32 or vice versa. As another example, acts 38 and/or act 40 are optional. In another example, one, none, or additional output acts (32, 34, 26) are provided. The acts are performed in the order shown or a different order. The acts may be performed automatically, manually, or combinations thereof.

In act 20, a medical ontology is provided. The medical ontology indicates one or more semantic groupings of features. The medical ontology is created by mining, extracting, training, manual input, machine learning, data transfer, or other process. The medical ontology is a publicly available or privately created ontology. A single ontology with or without changes may be used. A plurality of types of ontologies may be integrated into the medical ontology. For example, one or more levels include semantic groupings from a specific type of or specific one of medical ontologies. Biomedical data, information, and knowledge spanning any desired spectrum, such as from genetic to clinical to epidemiological, are integrated or included in the medical ontology. In one example, a medical ontology for a comprehensive view of a child's health is created. In other examples, the medical ontology is of a specific disease for all or for a class (e.g., adults). The medical ontology may be directed to improving individual disease prevention, screening, early diagnosis, therapy, and/or follow-up of diseases (heart, inflammatory, brain or other).

In the example of FIG. 4, the medical ontology is created for Atrial Septal Defect (ASD), which is characterised by a hole in the atrial septum. ASD is a congenital heart defect, is perhaps the most common cause of Right Ventricle Overload (RVO), and is among the most common paediatric heart diseases. Usually, the intervention to treat ASD is performed at a pre-school age (4-6 years of age). However, the size of the hole is constantly changing with time and in some cases the defect may get worse, so that time can be lost to do device closure (trans-catheterisation) and only an open-heart surgery can be performed. On the other hand, in some cases the hole in the septum (even a moderate-sized one, even at the age of 4-6) may close on its own. The phenomenon of ASD development is rather unclear to physicians and data-driven decision support by identifying similar previous patients for outcome correlation may assist in making the appropriate clinical decision.

Another example problem where decision support might be useful is possible complications after trans-catheterisation. There are cases where tissue erosion and rupture is reported, which might need another trans-catheterisation procedure, or even surgery. Distinguishing potentially high-risk patients in terms of possible complications after ASD treatment is another important task.

Using different examinations and tests, such as echocardiogram, chest X-ray, electrocardiogram, Doppler study, MRI, and cardiac catheterisation, a physician collects available information for determining the diagnose and the most suitable treatment. As the prognosis of ASD development depends on heterogeneous features of different kinds representing clinical data, genetic data, ECG, and imaging data, the resulting feature space becomes quite complex. The medical ontology represents the features in a hierarchical, semantic structure. By mapping and relating the concepts of the feature ontology to existing medical ontologies, valuable medical background knowledge, such as relations between concepts, constraints, and axioms can be used for refining the feature ontology. The refinement may improve the predictive performance of decision support.

In the example of FIG. 4, some branches are marked with different weights, reflecting the relative importance of corresponding features. The weights are arbitrary (e.g., an average), are based on machine learning and validation, are based on expert input, and/or are based on user adjustment. The weights can be fine-tuned by an expert or in an automated way using a machine learning technique (e.g., a genetic algorithm). Fine-tuning weights corresponding to different branches in the feature ontology for a particular problem may lead to the discovery of important problem-specific knowledge.

In one embodiment, the medical ontology is automatically created. A plurality of associated terms is identified from another medical ontology. A processor performs the identification, but the terms may be manually identified. The terms are identified from one or more ontologies. The associated terms may have different relationships with a term of interest, such as identifying the associated terms as having a IS-A type, cause, effect, symptom, sign, related disease, body location, drug, and/or morphology relationship. A plurality of terms of interest may be used. For example, two or more sets of terms associated with different terms of interest are identified. Overlapping terms are selected to form a set of desired associated terms. Each term of interest may be any type of data, such as disease, a morphology, or a term from any of the other relationship types described herein.

In one embodiment, given some concept or term of interest, all the sub-concepts consistent with the ontology are identified in a semantic grouping. It is assumed that sub-concepts imply the broader concept so that the concepts may be inferred from the sub-concepts. A concept is a term of interest and a sub-concept is related by an "IS A" or other indicative relationship. For example, a concept is heart failure. Sub-concepts may be cardio vascular disease, myopathy, or other more generic or more specific terms indicating heart failure. As another example, the concept "appendicitis" in the finding/disorder hierarchy in SNOMED is the term of interest. The attributes associated morphology, and finding site connects this concept to Inflammation and Appendix structure concepts of Body structure hierarchy respectively as non-IS A relationships. These terms may also be identified for possible use in the medical ontology.

The identification of associated terms may be restricted. For example, the distance in the medical ontology between the concept of interest and the current term is limited. The distance may be limited to any number of links, such as two. The limit may be different for different types of relationships, such as three of for IS A and only two for finding site. Other limitations may be alternatively or additionally provided, such as limiting the types of association or relationships.

In act 22, an algorithm is trained. A processor performs machine learning. The machine learns to identify at least one similar patient record from a set of patient records. Alternatively, probability, mining, or graphical modeling is performed, such as disclosed in U.S. Published Patent Application No. 2007/0094188. The training creates a machine-learnt algorithm.

The training incorporates domain knowledge from a medical ontology describing interrelations between features into the machine learning algorithm. A user manually constrains the machine learning based on the ontology. Alternatively, the machine learning automatically incorporates the medical ontology.

In one embodiment, the distance used for machine learning is redefined based on the medical ontology. The performance of machine learning may be improved by redefining the concept of similarity by incorporating constraints provided by ontological domain knowledge. Instead of simply providing a machine learning algorithm with features in the form of a single vector or a set of vectors, the features are semantically enhanced by integrating the graph structures of relevant domain ontologies. This can be achieved through the integration of all related ontological knowledge into a single ontology, systematically structurising the feature space.

Any ontology mapping to the machine learning algorithm may be used. Automated or manual processes may be used.

A processor trains the algorithm for distance or similarity searching. The associated terms from the medical ontology are applied to a training data set. The algorithm is learnt automatically by employing both training data (structured and/or unstructured), such as a collection of electronic medical records in a database, and the ontology, a representation that captures relationships that hold among the records or attributes in the database.

Relationships of the associated terms are determined by machine learning. Classification is learned for the features of the ontology. The algorithm is built by optimizing a function of both the training data and the associated constraints from the ontology. The relationships are calculated by observing sample data but also by automatically incorporating knowledge encoded in the ontology, reducing the need for manual expert intervention. In one embodiment, a variable is assigned to each associated term or feature. Each data point is represented as a random vector. In each vector, the entries or values for the variables can be missing or observed. The training data is constructed or treated as a plurality of vectors, each vector having a location for each of the variables. Any process may be used.

The training is performed in a single pass, or an iterative process is provided. Different combinations of some or all of the available variables from the selected set are tried. Different types of models, algorithms, training, or combinations thereof may be attempted. The best performing one or ones are assigned. Alternatively, a first sufficiently performing classifier is assigned and no further classifiers are built. In other embodiments, the different combinations or iterations are guided logically or based on a knowledge base. Any possible tuning may be provided, such as automated tuning and/or manual tuning based on information in the training data. The model may be applied to the training data for tuning.

By training, the optimal distance functions within the semantic constraints of the medical ontology are determined. All or only some of the associated terms from the medical ontology may be used. For example, the processor selects variables from the training set. The training set may not include the current patient record. Automated variable selection may be based on machine-learnt processes for variable selection and/or programmed identification. A leave-one-out approach may be used to identify variables associated with sufficient similarity distinction. Alternatively, manual input assists in selection of variables. The resulting similarity classifier characterizes the relationship between a set of variables representing concepts, sub-concepts, associated terms or entities of interest in a given domain.

In act 24, the semantic groupings are incorporated. The learning is a function of the one or more semantic groupings of features of the medical ontology. The features are organized into semantic groups, but one or more features may be outside of a grouping. The contribution of features and/or groups is limited based on the semantic grouping. A contribution of the features to a distance is constrained with the one or more semantic groupings. Aggregating features into a grouping contribution within each semantic grouping may avoid undesired over contribution from similar concepts. The distance for similarity learning is a function of the grouping contribution.

One of the most common machine learning techniques where similarity between instances is explicitly calculated is instance-based learning (e.g., k-nearest neighbour classification, k-NN). The distance function that lies in the core of k-NN is normally defined for a single set of unrelated features representing the problem. By semantically enhancing the set of relevant features by integrating medical domain knowledge and redefining the distance function, the patient diagnostic (classification) accuracy can be improved. The semantic groupings in the ontology may be used to constrain the learning in other algorithms.

In act 26, the multilevel grouping structure of the semantic groupings is used for learning. The semantic groups restrict the contribution of features in the learning. Each semantic grouping for a given level of the multilevel grouping structure has a relative contribution for the given level. This relative contribution constrains the learning. The graph structure of the medical ontology is integrated, limiting relative contributions at different levels. The features represent heterogeneous concepts. Each branch is for a type of data, such as clinical, imaging, ECG, and genetics. Different branches are for different types of data. The different branches include different sub-branches, providing multi-level integration for learning. In alternative embodiments, the medical ontology includes a single level of semantic groupings.

In act 28, the relative contribution of the semantic groupings, nodes, and/or features of the medical ontology are used for learning. FIGS. 4 and 5 show weights associated with different semantic groupings and/or features. The weights define the relative contribution to similarity provided by the grouping or feature. The distance function of the machine learning algorithm is defined by a distribution of weights as a function of the medical ontology. By weighting a contribution of each semantic grouping relative to the other semantic groupings in one or more levels, contributions may be optimized such that the at least one similar patient record is more similar.

A logical distribution of weights in the feature space may reflect the semantics of the domain. To give a simple example, imaging features should not outweigh clinical features just because their number can be more than a thousand. The imaging features are considered equally or relatively important for determining the distance if they are situated at the same level (horizontal in the examples of FIGS. 4 and 5) of the feature ontology. Relative contribution other than average may be used.

FIG. 5 shows a schematic distribution of weights in a feature ontology. The feature ontology is a hierarchical structure in the form of a tree graph, where the nodes $N_n^l$, where l is the level at which the node is situated and n is the ordinal number of the node at level l, correspond to a group of features with common semantics. The root node $N^0$ combines all the relevant features, and the leaves ($f_n^l$) include features. The tree structurises the feature space into k+1 levels. Leaves (features) can be situated at any level of the tree. In FIG. 5, the features are shown at level k+1 for the sake of simplicity.

The graph is weighted. Weights are assigned to the edges (i.e., branches of the tree). Weight $w_n^{lm}$ corresponds to the n-th child edge originating from the m-th node at level l. The weights of child branches of a node in such a feature ontology sum to one:

$$\sum_n w_n^{lm} = 1.$$

Any default distribution of weights for a given node may be used. For example, an average is provided (i.e., the weights of child branches are equal). Other default weights may be used, such as more heavily weighing certain types of semantic groupings (e.g., imaging).

The weight of a particular feature $f_n^l$ is defined as the product of the weights in the tree on the path towards this feature:

$$w(f_n^l) = \prod_{i=o}^{l-1} w_*^i(f_n^l),$$

where $w_*^i(f_n^l)$ is the weight of an ancestor branch of level i for feature $f_n^l$. According to this definition, the deeper a node (or a feature) is in the hierarchy, the less influence it has in the similarity assessment.

Rather than a default, the weights in the feature ontology may be established by an expert and/or fine-tuned with a machine learning algorithm (e.g. using a form of genetic search). The resulting feature weights may be used in combination with any distance function supporting feature weighting. In the simplest case, the overall distance is calculated as the weighted average of contributing partial distances corresponding to each relevant feature. Each partial distance may be different and may take into account the type and semantics of a particular feature but is normalised (i.e., in the range from 0 to 1). In alternative embodiments, different weighting schemes may be used.

In act 30, information derived from the learning is output. The information may be an indication of the results of learning, such as selected features or a notification of completion.

In another embodiment, the output information results from application in act 32 of the trained classifier (machine-learnt algorithm) to a medical record. A processor applies the trained algorithm. A patient record or data from a patient record are input. The algorithm is provided with a database of previous patient records or related data for searching in act 34. The previous data represents a sequence of instances where each instance is represented by at least one single feature vector describing the instance. The feature vector is multi-dimensional, such as including a plurality of features included in the medical ontology. The searching identifies distances between a current medical record and previous medical records.

The searching includes aggregating similarities in different groups. Similarities are calculated or similar records identified for each feature. For each semantic grouping, the similarities or distances for the features are aggregated. Aggregated similarities from different semantic groups may be aggregated in a multi-level approach.

One or more of the previous medical records are identified by the trained classifier. The identified records are the most or sufficiently similar previous patient records to the current patient record. The one or more similar instances may be used for clinical decision support. The identification and/or data from the similar previous patient records are output.

The information may be used to determine a prognosis, diagnosis, further testing, treatment or other information. For example, a class of similar patients may be examined to identify the treatment associated with the best outcome.

In act 36, information for validation is output, such as sensitivity. Any approach to validation may be used. In distance evaluation embodiments, the validation is based on expert-perceived similarity and/or automatic data-driven wrapper-like evaluation. For expert perception, a set of instances are ranked by a group of experts in a subject domain, according to the perceived similarity to another control instance. This process can be repeated for a number of control instances. The resulting rankings are compared with the one produced by the distance function under study. For example, Spearman's rank correlation coefficient is used for the comparison. The quality of the distance function is assumed to be proportional to the average expert-function rank correlation (the bigger the average correlation between the expert- and distance function-produced ranks the better). Inter-expert rank correlation may serve as a measure of expert agreement.

For data-driven evaluation, the distance function under study is used as an element in a learning algorithm that is used as a wrapper. The assumption is that the quality of the distance function is reflected by the performance of the learning algorithm on validation data. This approach may be applied for parameter selection and tuning in machine learning algorithms. The distance function is evaluated (or updated) in the context of the task being solved. For the example of FIG. 4, a good distance function should result in a better predictive performance (classification accuracy) of ASD classification. Any appropriate data-driven validation technique may be used in combination with an appropriate learning algorithm for wrapper-based distance evaluation. For example, cross validation together with k-NN classification is used. When enough data is available, this approach can be applied iteratively, to search for a better distance function in the space of valid distance functions.

In act 38, user input is received to alter the creation of the medical ontology, the learning, or the application. For example, the user adjusts the medical ontology. A new semantic grouping may be added, a feature may be moved between semantic groupings, or levels may be altered (e.g., a feature or grouping moved up or down a level). The incorporation or learning is re-performed as a function of the adjusted medical ontology.

As another example, the user alters relative weights, such as changing a semantic group weighting from 33% to 50%. Besides the improved predictive performance, the graph-based representation of the feature ontology may be convenient for an expert in order to establish different feature weights by changing the weights of branches corresponding to a certain semantic group of features, instead of assigning importance to each particular feature. The feature ontology can be presented to the expert as part of the system's graphical user interface and might provide an effective way for feature control and manipulation for decision support. The ontology is fixed or not be fixed. By allowing adjustment, the ontology is integrated as a flexible wrapper for more efficient machine learning and knowledge discovery. Changes in the feature ontology, initiated by the user and leading to an increase in machine learning performance, may also serve as an important source of novel knowledge in the subject domain.

The semantic groupings, multi-level arrangement, and weights of the medical ontology may improve performance of trained algorithms. Other information from medical ontologies may be useful. For example, the medical ontology includes a range for at least one feature. Normal value ranges for different standard medical features may be extracted from ontologies. Data with a value outside of the range is removed. The data is removed from the training data or the medical record of interest. The removal is before learning or during application of a machine-learned algorithm derived from the learning. The removal of outlying data may influence the distance metric.

As another example, the medical ontology may identify correlated or redundant features. Correlated or redundant features may have an influence on determining the inter-patient distance. In the example of FIG. 4, RV ED volume for MR imaging is noted as correlated with RV internal diameter for Ultrasound imaging. The blood volume of the right ventricle cavity can be determined using both ultrasound and magnetic resonance images. The estimate received with MRI is usually more exact, and the ultrasound estimate may be ignored when MRI information is available. Accordingly, the weight applied to the ultrasound feature is reduced or the feature is removed when the MRI feature is available. Conversely, if the MRI feature is not available, the weight of the ultrasound feature may be increased. Other correlations may be used.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for use of a medical ontology for computer assisted clinical decision support, the method comprising:
   providing a medical ontology indicating one or more semantic groupings of features;
   learning, by a processor, to identify at least one similar patient record from a set of patient records, the learning being a function of the one or more semantic groupings of features of the medical ontology; and
   outputting information derived from the learning.

2. The method of claim 1 wherein learning comprises integrating a graph structure of the medical ontology, the one or more semantic groupings of features corresponding to one or more respective branches of the graph structure.

3. The method of claim 2 wherein the features represent heterogeneous concepts, and wherein a first branch comprises a first type of data selected from the group of: clinical, imaging, ECG, and genetics, and a second branch comprises a second type of data selected from the group.

4. The method of claim 1 wherein learning as a function of the one or more semantic groupings comprises constraining a contribution of the features to a distance with the one or more semantic groupings.

5. The method of claim 4 wherein constraining comprises aggregating features into a grouping contribution within each semantic grouping, the distance being a function of the grouping contribution.

6. The method of claim 1 wherein learning as a function of the one or more semantic groupings comprises weighting a contribution of each semantic grouping relative to the other semantic groupings.

7. The method of claim 6 further comprising:
   receiving user input of the relative weighting;
   wherein weighting comprises weighting as a function of the user input of the relative weighting.

8. The method of claim 6 further comprising:
   optimizing contributions such that the at least one similar patient record is more similar.

9. The method of claim 1 wherein learning as a function of the one or more semantic groupings comprises learning from a multilevel grouping structure of the semantic groupings.

10. The method of claim 9 wherein each semantic grouping for a given level of the multilevel grouping structure has a relative contribution for the given level, the relative contribution constraining the learning.

11. The method of claim 1 wherein providing the medical ontology comprises combining a plurality of types of ontologies into the medical ontology, at least one of the one or more semantic groupings corresponding to different ones of the types of ontologies.

12. The method of claim 1 wherein learning comprises creating a machine-learnt algorithm, and wherein outputting comprises:
   applying the machine-learnt algorithm to a patient record;
   identifying the at least one similar patient record with the machine-learnt algorithm; and
   outputting an identification or data for the at least one similar patient record.

13. The method of claim 1 wherein outputting comprises outputting validation results.

14. The method of claim 1 wherein the medical ontology comprises a range for at least one feature;
   further comprising:
   removing data with a value for the at least one feature outside of the range before learning or during application of a machine learned algorithm derived from the learning.

15. The method of claim 1 wherein the medical ontology comprises an identification of correlated or redundant first and second features;
   further comprising:
   reducing a weighting and/or removing feature consideration of a first feature relative to a second feature.

16. A system for use of a medical ontology for computer assisted clinical decision support, the system comprising:
   a memory operable to store a machine-learnt algorithm, the machine-learnt algorithm integrating a multi-level medical ontology, the multi-level medical ontology having a hierarchal node structure defining relative contribution of features at different levels of the multi-level medical ontology; and
   a processor operable to apply the machine-learnt algorithm to a medical record of a patient.

17. The system of claim 16 wherein the machine-learnt algorithm is operable to identify a previous medical record similar to the medical record of the patient.

18. The system of claim 16 wherein the multi-level medical ontology includes features with common semantics for a first type of node and second types of nodes connected with at least a first type of node, and wherein the processor is operable to aggregate a contribution of the features for each of the first types of nodes, and aggregate a contribution of the contributions of the first types of nodes for each of the second types of nodes.

19. The system of claim 16 further comprising:
   a display operable to display a representation of the multi-level medical ontology, the display including weights for contributions of features and/or nodes.

20. In a computer readable storage media having stored therein data representing instructions executable by a programmed processor for computer assisted clinical decision support with a medical ontology using machine learning, the storage media comprising instructions for:
   incorporating, into a machine learning algorithm, domain knowledge from a medical ontology describing interrelations between features;
   searching, with the machine learning algorithm, a sequence of instances where each instance is represented by at least one single feature vector describing the instance, the searching including aggregating similarities in different groups, an aggregate similarity of at least one group being a function of an aggregate similarity of at least another group; and identifying, in response to the searching, a similar instance with the machine learning algorithm.

21. The instructions of claim 20 wherein incorporating comprises defining a distance function of the machine learning algorithm by a distribution of weights as a function of the medical ontology.

22. The instructions of claim 20 further comprising:

receiving user input adjusting the medical ontology; and re-performing the incorporation as a function of the adjusted medical ontology.

\* \* \* \* \*